(12) United States Patent
Rossi et al.

(10) Patent No.: US 8,980,940 B2
(45) Date of Patent: *Mar. 17, 2015

(54) STABLE CANNABINOID COMPOSITIONS AND METHODS FOR MAKING AND STORING THEM

(75) Inventors: Ronald Rossi, Forest, VA (US); Lee Jonathan Silverberg, Allentown, PA (US); Robert Hogan, West Grove, PA (US); Ramesh M. Shah, Voorhees, NJ (US)

(73) Assignee: Johnson Matthey Public Limited Company, London (GB)

( * ) Notice: Subject to any disclaimer, the term of this patent is extended or adjusted under 35 U.S.C. 154(b) by 6 days.

This patent is subject to a terminal disclaimer.

(21) Appl. No.: 13/302,289

(22) Filed: Nov. 22, 2011

(65) Prior Publication Data

US 2012/0263785 A1    Oct. 18, 2012

Related U.S. Application Data

(60) Continuation-in-part of application No. 13/237,388, filed on Sep. 20, 2011, now abandoned, which is a division of application No. 11/595,682, filed on Nov. 10, 2006, now Pat. No. 8,039,509.

(60) Provisional application No. 61/416,110, filed on Nov. 22, 2010.

(51) Int. Cl.
| | |
|---|---|
| A61K 31/35 | (2006.01) |
| A61K 31/353 | (2006.01) |
| A61K 9/48 | (2006.01) |
| A61K 47/10 | (2006.01) |
| A61K 47/12 | (2006.01) |
| A61K 47/44 | (2006.01) |
| C07D 311/80 | (2006.01) |

(52) U.S. Cl.
CPC ............. *A61K 31/353* (2013.01); *A61K 9/4858* (2013.01); *A61K 47/10* (2013.01); *A61K 47/12* (2013.01); *A61K 47/44* (2013.01); *C07D 311/80* (2013.01)
USPC .......................................... 514/453; 514/454

(58) Field of Classification Search
USPC .................................................. 514/453, 454
See application file for complete search history.

(56) References Cited

U.S. PATENT DOCUMENTS

| | | | |
|---|---|---|---|
| 6,403,126 B1 | 6/2002 | Webster et al. | |
| 7,186,850 B2 | 3/2007 | Silverberg | |
| 7,449,589 B2 | 11/2008 | Geiser et al. | |
| 7,674,922 B2 | 3/2010 | Burdick et al. | |
| 8,039,509 B2 | 10/2011 | Rossi et al. | |
| 8,383,842 B2 | 2/2013 | Gutman et al. | |
| 2004/0229939 A1 | 11/2004 | Chowdhury et al. | |
| 2005/0079136 A1 | 4/2005 | Woolfe et al. | |
| 2006/0160888 A1 | 7/2006 | Kottayil et al. | |
| 2007/0072939 A1 | 3/2007 | Kupper | |
| 2008/0112895 A1 | 5/2008 | Kottayil et al. | |
| 2008/0139644 A1 | 6/2008 | Rossi et al. | |
| 2008/0159961 A1 | 7/2008 | Woolfe et al. | |
| 2009/0181080 A1 | 7/2009 | Kottayil et al. | |

FOREIGN PATENT DOCUMENTS

| | | |
|---|---|---|
| JP | 2006504671 A | 2/2006 |
| WO | WO-99/32107 A1 | 7/1999 |
| WO | WO-02/096899 A1 | 12/2002 |
| WO | 2004016246 A1 | 2/2004 |
| WO | WO-2006/053766 A1 | 5/2006 |
| WO | WO-2006/063109 A2 | 6/2006 |
| WO | WO-2008/055922 A1 | 5/2008 |
| WO | WO-2009/020666 A1 | 2/2009 |

OTHER PUBLICATIONS

Chinese Office Action for Application No. 200780049596.2 dated Apr. 27, 2011.
U.S. Appl. No. 60/835,738 by Kottayil et al., filed Aug. 4, 2006.
Harvey, Stability of Cannabinoids in Dried Samples of Cannabis Dating from Around 1896-1905, *Journal of Ethnopharmacology*, 1990, vol. 28, pp. 117-128.
Turner et al., "Constituents of *Cannabis sativa* L. XVI. A Possible Decomposition Pathway of $\Delta^9$-Tetrahydrocannabinol to Cannabinol," *Journal of Heterocyclic Chemistry*, Dec. 1979, vol. 16, No. 8, pp. 1667-1668.
Munjal et al., "Polymeric Systems for Amorphous $\Delta^9$-Tetrahydrocannabinol Produced by a Hot-Melt Method. Part II: Effect of Oxidation Mechanisms and Chemical Interactions on Stability," *Journal of Pharmaceutical Sciences*, Nov. 2006, vol. 95, No. 11, pp. 2473-2485.

(Continued)

*Primary Examiner* — Renee Claytor

(74) *Attorney, Agent, or Firm* — RatnerPrestia

(57) ABSTRACT

A composition comprising a high purity cannabinoid, an acid, and a pharmaceutically-acceptable solvent achieves room temperature stability for over 24 months. The acid improves the stability of the composition and the solvent enhances the solubility of the acid, thereby allowing the acid to have an improved stabilizing effect on the highly pure cannabinoid. Preferably, the solvent is an alcohol and, more preferably, the composition contains an oil. A method for making the composition includes combining the cannabinoid and the solvent and evaporating a portion of the solvent, along with adding an acid to the composition, before, during, or after the evaporating step. A method for making and storing the composition includes storing the composition in a manner adapted to maintain its stability. Pharmaceutical dosage forms include a formulated composition, such as having the oil. A method of treating a subject comprises administering to the subject the dosage form.

32 Claims, No Drawings

(56) References Cited

OTHER PUBLICATIONS

Dajani et al., "1'-1'-Dimethylheptyl-Δ-8-tetrahydrocannabinol-11-oic Acid: A Novel, Orally Effective Cannabinoid with Analgesic and Anti-Inflammatory Properties," *The Journal of Pharmacology and Experimental Therapeutics*, 1999, vol. 291, No. 1, pp. 31-38.

International Search Report dated Jun. 22, 2012, from PCT International Application No. PCT/US2011/061803.

Solvay Pharmaceuticals Inc.: "NDA 18-651/S-021; MARINOL (Dronabinol) capsules," Sep. 2004.

Lindholst, "Long term stability of cannabis resin and cannabis extracts," *Australian Journal of Forensic Sciences*, vol. 42, No. 3, Jul. 2010, pp. 181-190.

Thakur et al., "Natural cannabinoids: Templates for drug discovery," *Life Sciences*, 2005, vol. 78, pp. 454-466.

Office Action for corresponding Japanese Patent Application No. 2009-535748 dated Dec. 11, 2012.

US 8,980,940 B2

STABLE CANNABINOID COMPOSITIONS AND METHODS FOR MAKING AND STORING THEM

This application is a non-provisional application claiming priority of U.S. Provisional Patent Application No. 61/416,110, filed Nov. 22, 2010, and is a continuation-in-part of U.S. patent application Ser. No. 13/237,388, filed Sep. 20, 2011, which is a division of U.S. patent application Ser. No. 11/595,682, filed Nov. 10, 2006, which issued as U.S. Pat. No. 8,039,509 on Oct. 18, 2011, the disclosures of all of which are incorporated herein by reference in their entireties for all purposes.

FIELD OF THE INVENTION

The present invention relates to compositions and products comprising at least one cannabinoid compound, such as (−)-$\Delta^9$-trans-tetrahydrocannabinol, methods for making and storing such compositions and products as well as improving their stability. The compositions have particular utility in pharmaceutical dosage forms for treating a variety of medical conditions.

BACKGROUND OF THE INVENTION

*Cannabis* is a genus of flowering plants that includes three putative species, *Cannabis sativa, Cannabis indica,* and *Cannabis ruderalis. Cannabis* has long been used for fibre (hemp), for medicinal purposes, and as a recreational drug.

Cannabinoid is a generic term for phytocannabinoids, endocannabinoids, and synthetic cannabinoids. Phytocannabinoids are the natural compounds found in the *Cannabis* plants. More than 60 cannabinoids have been isolated from *Cannabis* plants with tetrahydrocannabinol (THC), cannabidiol (CBD), and cannabinol (CBN) being the most prevalent natural cannabinoids. THC is the primary psychoactive component of the plant and has been used to treat a wide range of medical conditions. More specifically, THC binds to specific receptors in the brain called cannabinoid receptors and, in doing so, causes some pain reduction, may reduce aggression, can stimulate appetite, and helps reduce nausea.

CBD is not considered to be psychoactive but has been reported to relieve convulsions, inflammation, anxiety, and nausea. CBN is considered to be mildly psychoactive and is the primary product of THC degradation; thus, its concentration increases during storage as well as with exposure to light, heat, and air.

Endocannabinoids activate the cannabinoid receptors and are found in nervous and immune systems, while synthetic cannabinoids are a structurally diverse group of substances also capable of binding to cannabinoid receptors. Classical cannabinoids are considered to be a chemical class of synthetic cannabinoids that are structurally related to THC.

FIG. 1 from U.S. Pat. No. 7,449,589, incorporated herein by reference, shows various cannabinoid compounds including THC, CBD, and CBN. THC reportedly has at least eight individual isomers of which (−)-$\Delta^9$-trans-tetrahydrocannabinol ((−)-$\Delta^9$-trans-THC) is the main and most active isomer. Although $\Delta^8$-tetrahydrocannabinol has similar activity as (−)-$\Delta^9$-trans-THC, it is only approximately 75% as potent and also tends to degrade to other compounds including CBN. Several pharmaceutical products exist which contain either phytocannabinoids (natural) or synthetic cannabinoids. For example, dronabinol (Marinol®) is the International Nonproprietary Name (INN) for an encapsulated THC product which has been used therapeutically as an appetite stimulant, antiemetic, and analgesic, either as an inhalant or as an oral drug. Also, nabilone (Cesamet®) is a synthetic analog of dronabinol (Marinol®), while Sativex is a cannabinoid extract oral spray containing THC and other cannabinoids which is used to treat neuropathic pain and spasticity. Further, rimonabant (marketed under various tradenames) is a selective cannabinoid receptor antagonist used as an anti-obesity drug and as a smoking cessation. Several other cannabinoid-containing products exist and others will likely soon be marketed.

Thus, considering the therapeutic effect of compositions containing cannabinoids, especially (−)-$\Delta^9$-trans-THC, there is a continuing need for improving existing cannabinoid-containing products as well as a need for new products containing cannabinoids, especially in the pharmaceutical field.

WO 2006/063109, incorporated herein by reference, discloses an encapsulated THC composition including (−)-$\Delta^9$-trans-THC purportedly having improved stability. The WO '109 application emphasizes that stability can be improved by including bases (e.g., amines) in the formulation. In addition, the stability of the compositions of the WO '109 application is best preserved by storing the compositions in a sealed container, such as in a capsule, and under refrigerated conditions. More specifically, the WO '109 application asserts that one embodiment of the invention described therein overcomes the deficiencies of prior art oral dosage forms containing (−)-$\Delta^9$-trans-THC by utilizing hard gelatin capsules, instead of soft gelatin capsules. As stated in the application, unlike soft gelatin capsules, hard gelatin capsules do not contain glycerol, a major cause of instability for the active (−)-$\Delta^9$-trans-THC pharmaceutical ingredient. The WO '109 application purports to provide a stable product, such as one that does not degrade to an unacceptable extent during the desired shelf-life of the dosage form.

SUMMARY OF THE INVENTION

There continues to be a need for improving the stability of cannabinoid compounds, compositions, and products as well as methods for making and storing them. The present inventors have sought to improve the stability of such compounds, compositions, and products, especially as they relate to the (−)-$\Delta^9$-trans-THC isomer, and in so doing have developed improved methods for making and storing them. More specifically, the inventors have sought to provide a high purity pharmaceutical composition which includes the (−)-$\Delta^9$-trans-THC isomer and demonstrates improved stability characteristics.

Cannabinoid compositions according to the invention exist in various concentrations and forms. For example, a cannabinoid composition can exist as a dilute material (e.g., a composition comprising THC compounds with a major amount of one or more solvents); as a partially evaporated material (e.g., a composition comprising THC compounds with a reduced amount of one or more solvents after at least one evaporation stage); as a neat material (e.g., a composition comprising THC compounds with no solvent); or as a material for incorporation into various pharmaceutical forms (e.g., composition comprising THC compounds, solvent, and oil, and optionally other constituents, inside a pharmaceutical capsule). As a result, the concentration of THC will clearly differ based on the amount of other constituents present in the composition. The concentration of THC will also depend on the particular pharmaceutical dosage form in which the THC is incorporated.

The inventors have found that the addition of an acid improves the stability of cannabinoids, i.e., there is less degradation of cannabinoid, such as (−)-$\Delta^9$-trans-THC, during prolonged storage of composition comprising the cannabinoid under various storage conditions. Also, the inventors have discovered that the inclusion of a pharmaceutically-acceptable solvent, including in particular an alcohol, improves the solubility of the acid, thereby enabling it to more effectively stabilize the cannabinoid. Accordingly, an embodiment of the invention is a composition comprising: a cannabinoid, an acid, an oil, and at least one pharmaceutically-acceptable solvent wherein the solvent is present in a concentration of between about 0.001% by weight and about 15% by weight, and wherein the acid is sufficiently soluble in the solvent to provide an amount of dissolved acid in the solvent which improves the stability of the composition. In this embodiment, the oil typically comprises a majority of the composition, preferably at least 90% by weight of the composition.

According to another embodiment of the invention, the cannabinoid comprises $(-)-\Delta^9$-trans-THC, the oil comprises sesame oil, the solvent comprises ethanol, and the acid comprises citric acid, preferably wherein the amount of ethanol is sufficient to dissolve at least a portion of the citric acid such that the composition is stable at room temperature for 24 months. Preferably, for this embodiment, the amount of ethanol is between about 0.01% and about 10% by weight, more preferably between about 0.1% and about 2% by weight, most preferably less than or equal to about 0.5%.

Another embodiment of the invention provides a dosage form comprising: (a) a composition comprising a cannabinoid, an acid, an oil, and a pharmaceutically-acceptable solvent in a concentration of between about 0.001% by weight and about 15% by weight, wherein the acid is sufficiently soluble in the solvent to provide an amount of dissolved acid in the solvent which improves the stability of the composition; and (b) a capsule encapsulating the composition.

According to another embodiment of the invention, a method for making a composition comprises combining a cannabinoid and a pharmaceutically-acceptable solvent to provide a dilute product; evaporating a portion of the solvent from the dilute product; and adding an acid to provide the composition. Such compositions are stable and are suitable for storage, including under freezer conditions for later formulation into pharmaceutical dosage forms.

According to another embodiment of the invention, a method of making and storing a composition comprises combining a cannabinoid, an acid, and a pharmaceutically-acceptable solvent, wherein the acid is sufficiently soluble in the solvent to provide an amount of dissolved acid in the solvent which improves the stability of the composition.

According to another embodiment of the invention, a method for making a composition comprises combining a cannabinoid and a pharmaceutically-acceptable solvent to provide a dilute product; evaporating a portion of the solvent from the dilute product; and adding an acid and an oil to provide the composition. Such compositions are stable and are suitable for use as pharmaceutical dosage forms, for example by being encapsulated in a capsule.

Preferably, the compositions of the invention are highly pure. More preferably, the purity profile of the compositions by HPLC is no more than about 2.0% by weight of $\Delta^8$-THC; no more than about 0.5% by weight of cannabinol; no more than about 0.2% by mass of an impurity having a relative retention time (RRT) about 0.91 as determined by a validated impurities method described herein; no more than about 0.2% by area of individual unspecified impurities; and no more than about 2.5% total impurities.

The compositions are stored in a manner adapted to maintain the initial purity profile after exposure of the composition to storage conditions selected from the group consisting of: (i) refrigerated conditions of between about 5° C. to about 8° C. for 36 months; (ii) ambient conditions of about 25° C. and about 60% relative humidity for 24 months; (iii) elevated temperature conditions of about 40° C. and 75% relative humidity for nine months; and (iv) elevated temperature conditions of about 60° C. for 4 weeks. In an alternative embodiment, the composition is stored in freezer conditions and in a manner adapted to maintain the initial purity profile for 24 months.

According to another embodiment of the invention, a method of making and storing a composition comprises combining $(-)-\Delta^9$-trans-THC, a pharmaceutically-acceptable solvent, and an acid, wherein the composition has an initial purity of $(-)-\Delta^9$-trans-THC by HPLC of at least 97.5% by area. The composition is stored in a manner adapted to maintain the stability such that at least 95% by area of the $(-)-\Delta^9$-trans-THC remains in undegraded form after exposure of the composition to storage conditions selected from the group consisting of at least one of: (i) ambient conditions of about 25° C. and about 60% relative humidity for twelve months; and (ii) elevated temperature conditions of about 40° C. and 75% relative humidity for nine months.

Still another embodiment of the present invention is a method of treating a subject comprising administering to the subject a dosage form of the invention. The method comprises providing to the subject a therapeutically effective amount of the composition or product of the invention in order to treat one or more medical conditions suitable for treatment by administration of a cannabinoid.

Accordingly, embodiments of the present invention provide a stable composition comprising a therapeutically active cannabinoid, preferably $(-)-\Delta^9$-trans-THC. Embodiments of the invention provide such compositions that are stable at room temperatures for an extended period of time. Embodiments of the present invention are preferably refrigerated or encapsulated in a capsule in order to prevent significant degradation of cannabinoid, such as $(-)-\Delta^9$-trans-THC, over an extended period.

According to another embodiment of the invention, a composition comprises a cannabinoid, an acid, and a pharmaceutically-acceptable solvent in a concentration of between about 90% by weight and about 99% by weight, wherein the acid is sufficiently soluble in the solvent to provide an amount of dissolved acid in the solvent which improves the stability of the composition. Such a composition is suitable for being stored at freezer conditions for weeks, months, or years (e.g., 4 weeks, three months, six months, twelve months, or twenty-four months), and can later be subjected to evaporation and formulated into a pharmaceutical dosage form.

According to another embodiment of the invention, a composition consists essentially of a cannabinoid and an acid.

These and other embodiments and objects of the invention will become apparent upon further review of the specification and claims presented below. Thus, the above expressed embodiments and objects of the invention are not intended by the inventors to limit the scope of the invention.

DETAILED DESCRIPTION OF THE INVENTION

Cannabinoids, including especially THC, can be isolated from *Cannabis* plants or be made synthetically as described in, e.g., in U.S. Pat. No. 7,186,850, incorporated herein by reference. As $(-)-\Delta^9$-trans-THC is the most active isomer of THC, various techniques for isolating and separating the $(-)-\Delta^9$-trans-THC isomer from other compounds in THC have been developed. For example, U.S. Pat. No. 7,449,589 describes methods for purifying the (−)-Δ⁹-trans-THC isomer from a mixture of other THC isomers. However, THC, including in particular the (−)-Δ⁹-trans-THC isomer, is very unstable. Also, chemical synthesis and isolation of (−)-Δ⁹-trans-THC are both challenging. The (−)-Δ⁹-trans-THC isomer is very prone to acid-catalysed isomerization to the Δ⁸-THC isomer, is easily oxidized by oxygen to form inactive cannibinol, and is also sensitive to light and heat. All of these factors make it difficult to synthesize, purify, and store a high purity THC composition comprising the (−)-Δ⁹-trans-THC isomer which is stable over time and under various storage conditions.

Dissolving a cannabinoid in a solvent or carrier tends to improve (−)-Δ⁹-trans-THC's stability, but it is still usual to store a cannabinoid under refrigerated conditions, e.g., at about 5° C.-8° C., in an effort to minimize or prevent its degradation. Encapsulating a cannabinoid composition also improves its stability. The present invention provides a cannabinoid composition, especially a composition comprising the (−)-Δ⁹-trans-THC isomer. The present invention also provides improved methods for making and storing such compositions.

The inventors have found that the addition of an acid improves the stability of THC, i.e., there is less degradation of (−)-Δ⁹-trans-THC during prolonged storage of a THC composition under various storage conditions. Also, the inventors have discovered that the inclusion of a solvent, including in particular an alcohol, improves the solubility of the acid thereby enabling it to more effectively stabilize (−)-Δ⁹-trans-THC. Accordingly, a composition according to an embodiment of the invention comprises a cannabinoid, an acid, an oil, and a pharmaceutically-acceptable solvent in a concentration of between about 0.001% by weight and about 15% by weight, wherein the acid is sufficiently soluble in the solvent to provide an amount of dissolved acid in the solvent which improves the stability of the composition.

Compositions of this invention include without limitation a batch or mixture of cannabinoids, including the (−)-Δ⁹-trans-THC isomer in pure or substantially pure form, stored in a solvent before further formulation; a batch or mixture of formulated cannabinoids having all of the excipients combined therewith; a batch or mixture of partially formulated cannabinoids having some but not all of the excipients combined therewith; and the composition as it exists as a pharmaceutical final dosage form or product, such as in the form of a solution contained in a pharmaceutical capsule.

Cannabinoids suitable for use in the present invention include any cannabinoid suitable for pharmaceutical use. Many such cannabinoids are well-known, as described for example in the WO '109 application. Cannabinoids include derivatives, such as side chain alkyl derivatives including the 1,1 dimethylheptyl derivative mentioned in U.S. patent application Ser. No. 11/595,682 (U.S. Patent Application Publication No. 2008/0139644), incorporated herein by reference. Preferably, the cannabinoid is a tetrahydrocannabinol (THC) compound, most preferably, (−)-Δ⁹-trans-THC.

The amount of cannabinoid in the composition can be determined by an artisan based on the desired route of administration, the type of the desired final dosage form, the desired potency of the final dosage form, the activity of the particular cannabinoid being formulated, and the type of composition of the invention (e.g., a composition stored in a solvent before further formulation versus a final formulated dosage form having all of the excipients). As is described in U.S. Patent Application Publication No. 2004/0229939, incorporated herein by reference, the pharmacokinetics of THC varies with the route of administration. Thus, different dosage forms will require different amounts of THC to achieve equivalent psychological and physiological effects. Once these factors are determined, then an artisan can readily identify how much cannabinoid is required to achieve the desired concentration in the final dosage form.

In some embodiments, the concentration of the (−)-Δ⁹-trans-THC isomer in the composition is preferably from about 0.1% to about 15% by weight of the composition, more preferably from about 1% to 10% by weight, most preferably from about 3% to 7% by weight when the composition of this invention is directed to a batch or mixture of cannabinoids, an acid, and a partially evaporated solvent before formulation and use inside a capsule adapted for oral administration. On the other hand, when the composition of this invention has been further formulated to contain a second solvent, such as an oil, and optionally other excipients for inclusion in as the mixture inside of a pharmaceutical capsule, the amount of (−)-Δ⁹-trans-THC in the composition is preferably from about 4% to about 7% by weight of the composition, more preferably about 5% by weight, but, as stated above, these amounts could vary depending on the factors set forth above. The total amount of a dosage form will depend on the desired dose, and currently (−)-Δ⁹-trans-THC products exist at 2.5, 5, and 10 mg doses.

The composition of the invention also includes an acid which improves the stability of the composition. For example, the acid used in the composition of the invention may aid in inhibiting or serve to inhibit the degradation of the cannabinoid that is intended to be formulated, most typically (−)-Δ⁹-trans-THC. The composition further includes a pharmaceutically-acceptable solvent, described below, in which the acid is sufficiently soluble to provide an amount of dissolved acid in the solvent which improves the stability of the composition. The concentration of acid used may be less than, equal to, or greater than the solubility limit of the acid in the particular solvent chosen. The inventors have noticed the presence of some undissolved acid in compositions of the present invention, but this does not appear to adversely affect the stability of the compositions.

The acid may be a mineral acid such as phosphoric acid or an organic acid. Examples of suitable organic acids include, but are not limited to, citric acid, ascorbic acid, acetic acid, malic acid, oxalic acid, succinic acid, fumaric acid, salicylic acid, tartaric acid. More preferably, the suitable organic acids are citric acid, acetic acid, oxalic acid, succinic acid, salicylic acid, tartaric acid. Most preferably, the organic acid is citric acid. The composition may comprise a combination of different acids, optionally a combination of at least one organic acid with at least one mineral acid, more than one organic acid, or more than one mineral acid. Also, the acid may be a constituent of an ingredient of the composition. For example, the acid can be a free fatty acid or acids contained in an oil, such as sesame oil. Preferably, the acid in the oil is already dissolved therein, such that no additional solvent to enhance the solubility of the acid is required.

The acid or acids can be a strong acid, a weak acid, or both. However, if the amount or concentration of strong acid is too large, the (−)-Δ⁹-trans-THC isomer will quickly degrade. Thus, preferably, the acid is a weak acid as such acids seem to have an especially positive stabilizing effect on the (−)-Δ⁹-trans-THC isomer thereby forming a composition having improved stability. More preferably, the weak acid is selected from citric acid, ascorbic acid, oxalic acid, succinic acid, tartaric acid, acetic acid, lactic acid, salicylic acid, carbonic acid and phosphoric acid and mixtures thereof. Also, triprotic acids are generally more preferred than diprotic acids, which in turn are more preferred than monoprotic acids. Most preferably, the weak acid is citric acid.

The amount of acid will depend on such factors as the type of acid used, the particular THC composition being stored, the storage conditions, and the desired stability. A minimum amount of acid is that amount needed to improve the stability of the composition. For example, the inventors have found that, when a THC composition in ethanol is saturated with $CO_2$, the composition is very stable in both freezer and refrigerated storage conditions. Without being bound to any theory, it is the inventors' belief that this is a result of carbonic acid present in the ethanol saturated solution. Accordingly, the acid of the present invention could be carbonic acid formed as a result of sparging the ethanol and cannabinoid compound with carbon dioxide ($CO_2$) gas. Other acids may be formed in this way if a different solvent and a different sparging gas is used. The invention contemplates also adding a second or more acid (e.g., citric acid) in addition to forming carbonic acid in this manner.

Preferably, sufficient acid is added to a cannabinoid composition such that the composition, for example the $(-)$-$\Delta^9$-trans-THC isomer, is stable at about room temperature and ambient humidity conditions for at least 24 months and over a shorter period of time under accelerated or elevated temperature and/or humidity conditions, as described below. In most instances, including when the cannabinoid comprises a high percentage of the $(-)$-$\Delta^9$-trans-THC isomer and when the acid is citric acid, a sufficient concentration of the acid will be from about 0.1 ppm to about 10,000 ppm of the composition, more preferably from about 1 ppm to about 1000 ppm, and most preferably from about 10 ppm to about 100 ppm.

In a preferred embodiment of the invention, the composition includes a pharmaceutically-acceptable solvent in a concentration of between about 0.001% by weight and about 15% by weight of the composition when an oil is present. As mentioned above, a solvent is used to solubilize an amount of acid which improves the stability of the composition. The solvent is not water, although it might contain a small amount of water, such as that amount often included in certain alcohols, including ethanol. Nonetheless, the solvent would preferably have no water or very little water, such that the concentration of water in the composition is less than 2% by weight, preferably less than 0.5% by weight, and most preferably less than 0.1% by weight. In addition, the solvent is not an oil, although an oil is added as a second solvent (i.e., primarily as a solvent or carrier for the cannabinoid) in some embodiments of the invention, as described in detail below. Preferably, the solvent exists as a liquid at room temperature.

The solvent may be any pharmaceutically-acceptable solvent, namely a solvent which is not biologically undesirable or does not cause any undesirable effects to a subject when provided in the amount intended in the chosen dosage form to be administered. Such solvents may include, without limitation, $C_1$-$C_4$ alcohols and other suitable class 3 solvents as listed in the United States Pharmacopeia, and mixtures thereof. Preferably, the solvent is a $C_1$-$C_4$ alcohol selected from methanol, ethanol, propanol, iso-propanol and butanol, and most preferably ethanol. Often, the solvent selected is the same one used in upstream processing of the cannabinoid. For example, as described in U.S. Pat. No. 7,449,589, the composition comprising $(-)$-$\Delta^9$-trans-THC can contain ethanol as a result of an earlier separation or purification process utilizing supercritical fluid chromatography (SFC), and ethanol can be chosen as the solvent in the composition in the event that the purification process of the '589 patent is used.

As mentioned above, it appears that the solvent improves the solubility of the acid, thereby allowing the acid to improve the stability of the composition. Thus, in embodiments including a solvent, a minimum amount of solvent (e.g., ethanol) is that amount needed to dissolve an amount of acid necessary to improve the stability of the composition. Preferably, sufficient solvent is added such that the composition achieves room temperature stability for at least 24 months and over a shorter period of time under accelerated or elevated temperature and/or humidity conditions, as described below. Thus, in a preferred embodiment of the invention, the amounts of acid and alcohol are effective to provide sufficient dissolved acid in the composition to achieve room temperature stability for at least 24 months. As mentioned above, it has been found that it is not necessary to add sufficient alcohol to dissolve all of the acid as some acid remaining insolubilized in the composition does not appear to adversely affect stability. Preferably, the amount of solvent in the composition is from about 0.001% by weight to about 15% by weight, more preferably from about 0.01% by weight to about 10% by weight, still more preferably from about 0.1% by weight to about 1% by weight, and in some embodiments from 0.1% by weight to about 2% by weight, all when an oil is present. These numbers are provided specifically with citric acid, ethanol, sesame oil and $(-)$-$\Delta^9$-trans-THC in mind, but are applicable to other embodiments. In any event, the concentration of solvent could be readily determined based on the desired stability and the acid being used.

As described below, the composition of the invention containing primarily only three constituents (i.e., excluding oil) can be stored for some time prior to formulation without significant degradation. In particular, a composition according to this embodiment comprises a cannabinoid, an acid, and a pharmaceutically-acceptable solvent in a concentration of between about 90% by weight and about 99% by weight, wherein the acid is sufficiently soluble in the solvent to provide an amount of dissolved acid in the solvent which improves the stability of the composition. Preferably, the amount of solvent is about 92% to 98%. As shown in Example 1 below, compositions of this embodiment of the present invention can achieve a very high degree of stability when stored cold, such as less than 0° C., and more preferably in freezer conditions, such as between −15° C. and −30° C. After being stored for some time in this form, the composition of the present invention can be combined with pharmaceutically-acceptable excipients and formulated into a variety of dosage forms, including as a liquid or mixture for encapsulation inside of a capsule, as a solid for use as a tablet or a sublingual dosage form, and as a suspension for oral administration, among others.

As mentioned above, according to an embodiment of the present invention, the composition includes oil. Similar to alcohol, oil acts as a solvent or carrier for the cannabinoid. Various oils can be used effectively in the present invention including, but not limited to, vegetable oils, fish oils, or animal fats. Preferably, the oil is selected from the group consisting of: almond oil; babassu oil; borage oil; blackcurrant seed oil; canola oil; castor oil; coconut oil; corn oil; cottonseed oil; evening primrose oil; grape seed oil; groundnut oil; mustard seed oil; olive oil; palm oil; palm kernel oil; peanut oil; rapeseed oil; safflower oil; sesame oil; shark liver oil; soybean oil; and sunflower oil as well as combinations thereof. Such oils may be hydrogenated or partially hydrogenated.

Presently, USFDA standards currently require refined sesame oil be used in pharmaceutical products, including dronabinol. Thus, preferably, the oil is sesame oil, more preferably refined sesame oil. However, the inventors have found that the use of unrefined sesame oil is advantageous presumably because of the presence of weak acids, including fatty acids, present in the unrefined oil. In contrast, the inventors have also found that Croda's Super Refined™ sesame oil is not nearly as effective in preventing the degradation of (−)-$\Delta^9$-trans-THC as unrefined sesame oil. Thus, it appears that the refining process removes, not only undesirable impurities, but also desirable acids contained in the oil product. It may be even more desirable to partially refine an oil, such as sesame oil, in a way which maintains some or all of the weak acids but removes impurities and/or contaminants. Also, it is contemplated that other unrefined oils may have a similar affect on maintaining the stability of (−)-$\Delta^9$-trans-THC. Various grades of sesame oil are available commercially.

The percentage of oil in a final composition of the invention will, of course, depend on the amount of the other components of the composition and the desired end use of the composition. In a preferred embodiment in which the composition is suitable for use as the mixture inside of a capsule and has a (−)-$\Delta^9$-trans-THC isomer concentration of from about 3% to about 7% by weight, at least 90% by weight oil, preferably sesame oil, is included.

As stated above, the (−)-$\Delta^9$-trans-THC isomer is commercially available in a soft gelatin capsule as dronabinol sold under the trademark Marinol®. The solution in Marinol® capsules contains, in addition to the (−)-$\Delta^9$-trans-THC isomer, the following inactive ingredients or excipients: sesame oil, gelatin, glycerin, (glycerol), methylparaben, propylparaben, and titanium dioxide. Thus, the compositions of an embodiment of the present invention include, among others, a cannabinoid compound, an acid, at least one solvent, and at least one excipient often found in pharmaceutical compositions, all of which may be contained inside of a pharmaceutical capsule. For example, the composition may further comprise antimicrobial agents, such as methyl paraben or propyl paraben. The composition may further comprise preservatives such as alpha-tocopherol or butylated hydroxytoluene (BHT). The composition may further comprise antioxidants. The antimicrobial agents, preservatives and antioxidants may be used alone or in combination. Preferably, any additional excipients such as those identified comprise less than 2.5% by weight, preferably less than 1% by weight, of the composition.

In a preferred embodiment, a composition of the invention comprises the (−)-$\Delta^9$-trans-THC isomer; refined sesame oil; citric acid; ethanol; and additional excipients comprising less than about 1% by weight of the composition. In an especially preferred embodiment, the amounts of these various components in the composition are about 4% to about 7% by weight of the (−)-$\Delta^9$-trans-THC isomer; about 93% to about 97% by weight of refined sesame oil; about 1 ppm to about 1,000 ppm citric acid; and about 0.05% to about 2% by weight ethanol.

Stability data obtained under accelerated conditions can be extrapolated; that is, known data obtained under accelerated conditions can be used to infer information about future data that has not yet been obtained. In fact, the U.S. Food and Drug Administration's Office of Generic Drugs has presented its thoughts on stability requirements for an existing drug substance to be stored at room temperature conditions at a minimum of three months of accelerated data and three months of room temperature data on one primary batch at the time of submission. See Regulatory Requirements for Stability Testing of Generics, AAPS Workshop, September 2007. Thus, it may be appropriate to extrapolate from accelerated data for a drug substance like the (−)-$\Delta^9$-trans-THC isomer which is intended to be stored at room temperature when there is no significant change under accelerated conditions. Moreover, according to the USFDA, if the accelerated and long term data exhibit little or no variability and/or change over time, the proposed retest period can be extrapolated up to twice as long as, but not more than 12 months beyond, the period covered by long-term data.

With this in mind, the following four storage conditions are grouped together herein: (i) refrigerated conditions of between about 5° C. to about 8° C. for three years; (ii) ambient conditions of about 25° C. and about 60% relative humidity for 24 months; (iii) elevated temperature conditions of about 40° C. and 75% relative humidity for nine months; and (iv) elevated temperature conditions of about 60° C. for four weeks. As can be seen, as the temperature increases, the storage time decreases. When no humidity control is provided, then the humidity can be approximated to be that of the surrounding environment. Similarly, the following two storage conditions are grouped together herein: (i) ambient conditions of about 25° C. and about 60% relative humidity for twelve months; and (ii) elevated temperature conditions of about 40° C. and 75% relative humidity for nine months.

The U.S. Pharmacopeia (USP) sets forth a monograph of dronabinol which requires a purity of at least 95% of the (−)-$\Delta^9$-trans-THC isomer and no more than 5.0% of total impurities. Other HPLC limits set forth in the USP monograph for dronabinol are shown in the following table:

| Name | Relative Retention Time | Relative Response Factor | Limit (% area) |
|---|---|---|---|
| Cannabinol | 0.78 | 2.7 | 1.5 |
| D9-Tetrahydrocannabinol | 1.00 | 1.0 | — |
| Exo-tetrahydrocannabinol[1] | 1.07 | 0.92 | 0.5 |
| D8-Tetrahydrocannabinol | 1.18 | 0.90 | 2.0 |
| Any other individual impurity | — | 1.0 | 1.0 |

[1](6aR, 10aR)-6,6-Dimethyl-9-methylene-3-pentyl-6a,7,8,9,10,10a-hexahydro-6H-benzo[c]chromen-1-ol.

In addition to limits set forth in the USP monograph for dronabinol, degradation limits have also been promulgated by the International Conference on Harmonisation of Technical Requirements for Registration of Pharmaceuticals for Human Use (ICH). These limits are as follows:

| Maximum Daily Dose | Threshold |
|---|---|
| <1 mg | 1.0% or 5 µg total daily intake (TDI), whichever is lower |
| 1 mg-10 mg | 0.5% or 20 µg TDI, whichever is lower |
| >10 mg-2 g | 0.2% or 2 mg TDI, whichever is lower |
| >2 g | 0.10%. |

See, e.g., ICH Q3BR Guideline, *Impurities in New Drug Products* (ICH Step 4). Thus, for example, when a new drug product will have a maximum daily dose from more than 10 milligrams to 2 grams, the threshold level of any degradation product is 0.2% by weight or 2 milligrams total daily intake (TDI), whichever is lower.

Based on the limits set forth in the USP and promulgated by ICH, an impurity specification by HPLC was established as follows:

NMT about 2.0% by weight $\Delta^8$-THC;
NMT about 0.5% by weight CBN;
NMT about 0.2% by mass of the impurity having a relative retention time of 0.91;
NMT about 0.2% by area for any individual unspecified impurity; and NMT about 2.5% total impurities (specified by weight or mass and unspecified by area).

All of these percentages are given in terms of a percentage based on the total weight, mass, or area of all THC compounds and impurities or degradation products thereof, not the total weight, mass, or area of the composition. The weight percentages of $\Delta^8$-THC and CBN were obtained by the well-known USP assay for THC in ethanol and by dividing the percent peak area determined by the HPLC method used herein by the analyte's known relative response factor. The chemical structure of the impurity having a relative retention time of 0.91 could not be determined, so its mass percentage was used, namely by dividing the percent peak area determined by the HPLC method used herein by the analyte's relative response factor, which was determined to be about 4 by an ESA Ultra Charged Aerosol Detector (CAD). For any other individual unspecified impurity or degradation product having some other relative retention time, the raw data provided by HPLC (i.e., percent peak area) was used. Consequently, it should be recognized that the upper limit of NMT 2.5% total impurities represents a combination of values having different units but, nonetheless, provides an important limit and representation of the purity and stability of the composition.

In addition, the $(-)$-$\Delta^9$-trans-THC isomer is more stable in an alcohol compared to when the alcohol is evaporated to provide a neat material (i.e., THC compounds with no solvent). However, in carrying out the USP assay method for THC, a starting material of THC in ethanol must be evaporated to a neat material. It is noted that up to 2.5% by weight degradation has been measured using HPLC during this evaporation step to yield neat material. The evaporation step to neat material is to determine a w/w % assay of delta-9 THC. This sample is evaporated under a stream of nitrogen; however, it is not totally an inert environment. The degradation can be measured by first injecting the THC in ethanol solution and obtaining an area percent result and then measuring the area percent again after the sample has been evaporated. A suitable correction has been applied to Example 7 below. This degradation should be minimal if the atmosphere during the evaporation step was more inert and if citric acid is added prior to evaporation of the sample.

Thus, a composition purity profile has been established as follows: no more than about 2.0% by weight of $\Delta^8$-THC; no more than about 0.5% by weight of cannabinol; no more than about 0.2% by mass of the impurity having a relative retention time of about 0.91; no more than about 0.2% by area of individual unspecified impurities; and no more than about 2.5% total impurities by summing the percent weights of $\Delta^8$-THC and cannabinol, the percent mass of the impurity having a relative retention time of 0.91, and the percent areas of the individual unspecified impurities. Based on the examples provided below, a process for making and purifying and isolating the $(-)$-$\Delta^9$-trans-THC isomer is known, but the invention provides a composition and method for storing the composition in a way which allows the composition to maintain this purity profile over a variety of storage conditions, namely: (i) refrigerated conditions of between about 5° C. to about 8° C. for three years; (ii) ambient conditions of about 25° C. and about 60% relative humidity for 24 months; (iii) elevated temperature conditions of about 40° C. and 75% relative humidity for nine months; and (iv) elevated temperature conditions of about 60° C. for four weeks. It should be appreciated that while the five-limit purity profile stated above is developed primarily with the $(-)$-$\Delta^9$-trans-THC isomer in mind, it is also suitable for use when other cannabinoids are the desired cannabinoid to be produced, with the exception that if the cannabinoid being produced is one of the first three listed, then that limit would not apply. For example, if the cannabinoid being produced is $\Delta^8$-THC, then the limit of NMT about 2.0% by weight $\Delta^8$-THC would not be applicable to that compound's purity profile, of course.

A preferable, and more stringent, purity profile can be achieved which is roughly one-half of the limits provided above, namely: no more than about 1.0% by weight of $\Delta^8$-THC; no more than about 0.2% by weight of cannabinol; no more than about 0.1% by mass of the impurity having a relative retention time of 0.91; no more than about 0.1% by area of individual unspecified impurities; and no more than about 1.5% total impurities by summing the percent weights of $\Delta^8$-THC and cannabinol, the percent mass of the impurity having a relative retention time of 0.91, and the percent areas of the individual unspecified impurities.

Another way of viewing a composition's stability is to identify first the composition's initial purity by using peak area from the HPLC data based on the peak area of the cannabinoid compound desired to be produced compared to the total area of all cannabinoids, namely that of the cannabinoid compound desired to be produced and impurities thereof. Then, after exposing the composition to certain storage conditions, the same measurements are made, but included in the denominator of determining purity are peak areas contributed by degradation products. Thus, the later measurement provides an indication of the percentage of the cannabinoid desired to be produced, e.g., $(-)$-$\Delta^9$-trans-THC, that remains in undegraded form after exposure of the composition to certain storage conditions. As provided below in Examples 1, 5, and 6, embodiments of the present invention have an initial purity of $(-)$-$\Delta^9$-trans-THC by HPLC of at least about 97.5% by area and a stability such that at least about 95% by area of the $(-)$-$\Delta^9$-trans-THC remains in undegraded form after exposure of the composition to storage conditions selected from the group consisting of at least one of: (i) ambient conditions of about 25° C. and about 60% relative humidity for twelve months; and (ii) elevated temperature conditions of about 40° C. and 75% relative humidity for nine months. According to preferred embodiments of the invention, the initial purity of $(-)$-$\Delta^9$-trans-THC by HPLC is at least about 99% by area (most preferably, 99.5%) and the stability is such that at least about 97.5% by area of the $(-)$-$\Delta^9$-trans-THC remains in undegraded form after exposure of the composition to either of these storage conditions.

According to an embodiment of the invention, a composition comprises $(-)$-$\Delta^9$-trans-THC, sesame oil, a solvent comprising ethanol, and citric acid, wherein the amount of ethanol is sufficient to dissolve at least a portion of the citric acid such that the composition is stable at room temperature for 24 months. In this context, stable shall mean a combination of both the five-limit purity profile mentioned above (i.e., NMT about 2.0% by weight $\Delta^8$-THC, etc.) and the undegraded form limit (i.e., at least 95% by weight of the $(-)$-$\Delta^9$-trans-THC remains in undegraded form after exposure to ambient conditions (e.g., about 25° C. with no humidity control).

As can be appreciated, compositions of the present invention can be formulated into a variety of dosage forms, either before or after some storage period. For example, a composition comprising the $(-)$-$\Delta^9$-trans-THC isomer, ethanol, and citric acid can be mixed with excipients to form an orally-administered liquid suspension or solution or could be mixed with excipients to form the composition which is used to fill capsules. The capsule may be a hard capsule or a soft capsule, such as the soft gelatin capsule used as part of the pharmaceutical product sold under the trademark Marinol®. According to an embodiment of the invention, a pharmaceutical dosage form or product comprises: (a) a composition comprising a cannabinoid, an acid, an oil, and a pharmaceutically-acceptable solvent in a concentration of between about 0.001% by weight and about 15% by weight, wherein the acid is sufficiently soluble in the solvent to provide an amount of dissolved acid in the solvent which improves the stability of the composition; and (b) a capsule encapsulating the mixture. According to another embodiment of the invention, a pharmaceutical dosage form or product comprises: (a) a composition comprising $(-)-\Delta^9$-trans-THC, sesame oil, a solvent comprising ethanol, and citric acid, wherein the amount of ethanol is sufficient to dissolve at least a portion of the citric acid such that the composition is stable at room temperature for 24 months; and (b) a capsule encapsulating the mixture.

According to another embodiment of the invention, a method for making a composition comprises combining a cannabinoid and a pharmaceutically-acceptable solvent to provide a dilute product; evaporating a portion of the solvent from the dilute product; and adding an acid to provide the composition. In this form, the composition may be stored for some time and can be stored cold as permitted by the solvent (e.g., less than about 10° C.) or even in freezer conditions (e.g., between about −15° C. to about −30° C.). After some time in storage at these conditions, for example between a week and six months, the composition may be formulated into a dosage form, such as a liquid for use in the inside of an orally-administered capsule.

According to another embodiment of the invention, a method for making a composition comprises combining a cannabinoid and a pharmaceutically-acceptable solvent to provide a dilute product; evaporating a portion of the solvent from the dilute product; adding an acid; and adding an oil to provide the composition. This method contemplates various methods, including a method in which the final composition is an entire or part of a dosage form, such as the liquid for use in the inside of an orally-administered capsule. The oil may be added promptly or after a delay of days, weeks, months, or even years. The composition prior to the oil being added is preferably stable, more preferably stable at ambient or room temperature conditions for at least 24 months. Alternatively, all of the constituents could be added initially, to either prepare individual dosage forms which could be stored individually or a batch of material for use in later formulation. If the composition includes the oil initially, then the composition could be stored cold, but typically not as cold as if only the solvent, such as ethanol, is present with the acid.

In the first step of the embodiment described above, combining a cannabinoid and a pharmaceutically-acceptable solvent to provide a dilute product can be accomplished in a number of ways. The step contemplates merely providing a cannabinoid and a pharmaceutically-acceptable solvent as a mixture from a prior synthesis, purification, or extraction step. In addition, an embodiment of the invention further comprises, before the combining step, obtaining a crude cannabinoid mixture. The crude cannabinoid composition may be obtained, for example, by carrying out the synthesis steps set forth in U.S. Pat. No. 7,186,850, incorporated herein by reference. Alternatively, the crude THC composition may be obtained by extracting the crude THC composition from *cannabis saliva* L, as described, for example, in U.S. Pat. No. 6,403,126, incorporated herein by reference. A further embodiment of the invention comprises, after the crude cannabinoid composition is obtained but before the combining step, purifying the crude cannabinoid composition to provide the cannabinoid for combining with the solvent, which includes the cannabinoid combined or mixed with the solvent upon purification. As an example, such purification can be effected according to the teachings of U.S. Pat. No. 7,449,589, also incorporated herein by reference.

The acid may be added before, during, or after the evaporating step. In an embodiment of the invention, the evaporating step comprises a first evaporating stage and a second evaporating stage, and the acid is added between the first evaporating stage and the second evaporating stage. As used herein, evaporating a portion of the solvent means evaporating less than all of the solvent contained in the cannabinoid and solvent mixture of the dilute product. The inventors have now recognized that at least one solvent, especially a $C_1$-$C_4$ alcohol, improves the solubility of the acid, thereby permitting the acid to improve the stability of the composition. In addition, it is also believed that refraining from allowing the cannabinoid to be in a neat (i.e., solvent-free) environment throughout the method of making and storing the composition is preferable in that it reduces the extent of degradation of the cannabinoid. Thus, by refraining from carrying the evaporating step through to completion, the inventors have elegantly maintained some solvent in the composition, allowing for the acid to stay in solution and for the solvent to reduce the degradation of the cannabinoid.

The amount of solvent initially combined or mixed with the cannabinoid in the dilute product is often determined by the synthesis of the cannabinoid and subsequent purification of the synthesized cannabinoid composition. While it is important at all times to ensure the cannabinoid composition are not exposed to oxygen, it is unnecessary to specify a particular amount of the solvent and, instead, it can be present at any range before evaporation. Any known procedure may be employed to evaporate a portion of the solvent comprising the at least one $C_1$-$C_4$ alcohol such as, but not limited to, vacuum distillation, rotary evaporation, thermal evaporation, vacuum centrifuge, and gaseous blow down. For example, the evaporating step is preferably carried out to an extent to reduce the amount of the solvent in the composition to about 0.001% by weight and about 15% by weight (presuming oil is present), with preferable ranges as set forth above. If the evaporating step is carried out in stages, any extent of evaporation may be effected in the first stage with the remainder in the second or subsequent stages. As mentioned above, either before evaporating, during evaporating (e.g., between two evaporation stages), or after evaporating, an acid is added to the composition in the solvent, preferably while it is maintained cold (e.g., less than 10° C., preferably less than 0° C., and most preferably at about −20° C.) and protected from light. In fact, it has been found advantageous to maintain the composition from getting too hot during the entire method for making. For example, the composition may be maintained at a temperature below 35° C., preferably less than 20° C., more preferably less than 10° C., still more preferably less than 0° C., and most preferably at about −20° C. throughout. An acid as discussed above may be added directly into the mixture. Instead of an acid being added, it can be formed in the mixture, for example by sparging $CO_2$ in the mixture to form carbonic acid. The purpose of sparging, therefore, may be two-fold, namely to drive off any oxygen and also to form carbonic acid. An artisan would readily recognize the extent to which the sparging should occur to achieve one or both of these purposes, as is desired for the particular application. In an embodiment, sparging the ethanol with $CO_2$ helps keep oxygen out, in addition to adding acidity to the composition. Applicants have found that a mixture of the $(-)-\Delta^9$-trans-THC isomer in ethanol that has been sparged with $CO_2$ prior to packaging results in a stable product (i.e., minimal degradation of the highly pure isomer) for at least 24 months under freezer conditions.

Alternatively, or in addition to the sparging, an acid may be added to the composition. As mentioned above, the minimum amount of acid is that amount needed to improve the stability of the composition. Preferably, sufficient acid is added or formed such that the composition achieves room temperature stability for at least 24 months. Any acid described above, preferably citric acid, may be added.

Other alternatives regarding the order of addition may be carried out. For example, the acid may be added to any of the other constituents either as a separate component, or the acid may be formed in a solution of the other constituents. As mentioned above, an example of the latter is the use of dissolved $CO_2$ in ethanol, which also stabilizes the $(-)$-$\Delta^9$-trans-THC isomer, probably due to formation of carbonic acid. Therefore, while the composition recites three constituents in many embodiments, it should be recognized that acid may be either added separately or formed by a reaction with other components and some additional constituent or may be an inherent part of one of the other constituents (e.g., free fatty acids of unrefined sesame oil). More specifically, compositions according to the invention may be prepared by adding the acid to a solution of a cannabinoid compound in sesame oil or a $C_1$-$C_4$ alcohol and mixing. Solutions comprising the $(-)$-$\Delta^9$-trans-THC isomer in sesame oil may be prepared by dissolving highly pure $(-)$-$\Delta^9$-trans-THC isomer in sesame oil, or by mixing sesame oil with a solution of the $(-)$-$\Delta^9$-trans-THC isomer in ethanol, and then distilling off a portion or all of the ethanol. When the solvent comprises the $C_1$-$C_4$ alcohol and an oil is added, the order of addition may vary, but preferably is: (1) evaporate to a certain extent; (2) add acid (e.g., citric acid) to a highly pure THC composition in $C_1$-$C_4$ alcohol solution; (3) add oil and optionally other additives such as methyl paraben, propyl paraben, BHT, and alpha-tocopherol; and (4) evaporate another portion of the $C_1$-$C_4$ alcohol to the desired amount (e.g., between about 0.1% by weight to about 1% by weight, or preferably less than about 0.5% by weight). As another alternative, when the solvent comprises ethanol and an oil is added, the THC in ethanol solution described above can be added to degassed USP/NF quality refined sesame oil containing an added acid dissolved in ethanol. In some formulations the sesame oil is blended first with methyl paraben, propyl paraben, BHT, and alpha-tocopherol.

According to yet another embodiment of the invention, a method of making and storing a composition comprises: combining a cannabinoid, an acid, an oil, and a pharmaceutically-acceptable solvent in a concentration of between about 0.001% by weight and about 15% by weight, wherein the acid is sufficiently soluble in the solvent to provide an amount of dissolved acid in the solvent which improves the stability of the composition, wherein the composition has an initial purity profile by HPLC of no more than about 2.0% by weight of $\Delta^8$-THC; no more than about 0.5% by weight of cannabinol; no more than about 0.2% by weight of the impurity having a relative retention time of 0.91; no more than about 0.2% by area of individual unspecified impurities; and no more than about 2.5% total impurities by summing the percent weights of $\Delta^8$-THC, cannabinol, and the impurity having a relative retention time of 0.91 and the percent areas of said individual unspecified impurities; and storing the composition in a manner adapted to maintain the initial purity profile after exposure of the composition to storage conditions selected from the group consisting of: (i) refrigerated conditions of between about 5° C. to about 8° C. for three years; (ii) ambient conditions of about 25° C. and about 60% relative humidity for 24 months; (iii) elevated temperature conditions of about 40° C. and 75% relative humidity for nine months; and (iv) elevated temperature conditions of about 60° C. for four weeks.

According to yet another embodiment of the invention, a method of making and storing a composition comprises: combining $(-)$-$\Delta^9$-trans-THC, a pharmaceutically-acceptable solvent, an oil, and an acid, wherein the composition has an initial purity of $(-)$-$\Delta^9$-trans-THC by HPLC of at least about 97.5% by area; and storing the composition in a manner adapted to maintain the stability such that at least about 95% by area of the $(-)$-$\Delta^9$-trans-THC remains in undegraded form after exposure of the composition to storage conditions selected from the group consisting of at least one of: (i) ambient conditions of about 25° C. and about 60% relative humidity for twelve months; and (ii) elevated temperature conditions of about 40° C. and 75% relative humidity for nine months.

According to yet another embodiment of the invention, a method of making and storing a composition comprises: combining a cannabinoid, an acid, and a pharmaceutically-acceptable solvent, wherein the acid is sufficiently soluble in the solvent to provide an amount of dissolved acid in the solvent which improves the stability of the composition, wherein the composition has an initial purity profile by HPLC of no more than about 2.0% by weight of $\Delta^8$-THC; no more than about 0.5% by weight of cannabinol; no more than about 0.2% by weight of the impurity having a relative retention time of 0.91; no more than about 0.2% by area of individual unspecified impurities; and no more than about 2.5% total impurities by summing the percent weights of $\Delta^8$-THC, cannabinol, and the impurity having a relative retention time of 0.91 and the percent areas of said individual unspecified impurities; and storing the composition in freezer conditions and in a manner adapted to maintain the initial purity profile for 24 months.

Certain improvements to handling and storing the composition are part of the invention. Along with the other advantages described herein, these improvements aid in the stability of the composition. For example, storing is preferably carried out by placing the composition in bottles and filling the bottles until the bottles are about full with the composition under an inert atmosphere (e.g., argon or nitrogen). It is preferred that the bottles be filled as much as possible (e.g., to the top or upper lip of the bottle) as this reduces the chance for oxidation by air. Preferably at least about 95% by volume of the bottle is filled, more preferably at least about 99%, even more preferably at least about 99.5%, most preferably at least about 99.9%. The composition of the bottles may be any material or materials which are known in the art to be air impermeable. Preferably, the bottles are made of glass, more preferably borosilicate. An example of a suitable bottle is the Pyrex® low actinic bottle commercially available from Corning, Inc. (Lowell, Mass.). Also, the inventors have found that the use of certain types of bottle caps improves the stability of the composition. The inventors believe this is because certain materials are more effective than others in establishing an oxygen barrier to the composition. Ideally, the caps used to cover the bottles establish an absolute oxygen barrier to the composition.

In yet another method of the present invention, a method of storing the pharmaceutical compositions and products described herein comprises placing the compositions in at least one of a capsule or a capped bottle and then into an impermeable and sealable bag with or without an oxygen absorbent material. Preferably, the composition is placed in a capsule which is placed in a glass bottle which is placed in an impermeable bag containing absorbent material. Most preferably, the capsule, bottle and bag are all sealed to prevent oxygen and other gases from contacting the composition. Preferably, the bags are capable of being vacuum sealed and are first vacuum sealed before receiving the bottle or capsule. Preferably, the material of the bag comprises biaxially-oriented polyethylene terephthalate. Examples of suitable bags include Mylar® bags, Mylar® foil bags and Pakdry 1500 bags commercially available from IMPAK Corp. (SorbentSystems.com) (Los Angeles, Calif.). Even more preferably, the bags contain an oxygen absorbent such as oxygen absorber packets commercially available from IMPAK Corp.

Preferably, throughout the method for making and storing, the temperature of the composition is not permitted to get too hot, and the composition is protected from light. For example, preferably the composition is maintained at a temperature below 35° C., preferably less than 20° C., more preferably less than 10° C., still more preferably less than 0° C., and most preferably at about −20° C. throughout.

As mentioned above, methods for making and storing a composition according to the invention comprise storing the composition in a manner adapted to maintain certain stability profiles or criteria. It should be recognized that any combination or all of the strategies described herein and other strategies can be used individually or combined in a manner to achieve the desired stability. An artisan would recognize the various strategies of storage for improving stability. Preferably, all of the strategies for improving stability during storage are implemented.

According to another embodiment of the present invention, a method of treating a subject in need of treatment with a cannabinoid comprises administering to the subject a dosage form as described herein. The subject could have any need known medically to be treated by administration of a cannabinoid, including a need for pain reduction, reduced aggression, stimulated appetite, and reduced nausea.

According to another embodiment of the present invention, a composition consists essentially of a cannabinoid and an acid. The present inventors have continuously sought to improve the stability of compositions containing (−)-$\Delta^9$-THC and $\Delta^8$-THC, as evidenced in their previous patent application PCT/EP2007/062174, which claimed a composition comprising:
  (a) a tetrahydrocannabinol compound chosen from $\Delta^8$ tetrahydrocannabinol, (−)-$\Delta^9$-trans-tetrahydrocannabinol and side chain alkyl derivatives of either compound,
  (b) a solvent chosen from oils and $C_1$-$C_4$ alcohols, and
  (c) an acid.
However, surprisingly, the inventors have since found that a composition that does not include a solvent may also ensure the stability of (−)-$\Delta^9$-THC and $\Delta^8$-THC. Accordingly, the present invention provides a composition consisting essentially of, or merely consisting of, a cannabinoid and an acid. The inventors have found that the addition of the acid improves the stability of the composition, i.e. there is less degradation of the cannabinoid compound during prolonged storage of the composition.

The acid used in the composition may be any acid described herein, but preferably is an organic acid, most preferably citric acid. Alternatively, a mineral acid may be used, and may be chosen from phosphoric acid, hydrochloric acid, nitric acid and sulphuric acid. In one embodiment the composition comprises a combination of different acids, optionally a combination of at least one organic acid with at least one mineral acid. Weak acids have an especially positive stabilizing effect on (−)-$\Delta^9$-trans-THC and its derivatives, forming a stabilized composition. If the amount or concentration of strong acid is too large, the $\Delta^9$-isomer degrades to the $\Delta^8$-isomer.

According to this embodiment, the amount of acid preferably ranges from about 0.05 to about 5% as a weight percentage of the composition, preferably from about 1 to about 2%. The amount of the cannabinoid in the composition is preferably from about 90 to about 99.95% as a weight percentage of the composition, preferably from about 95 to about 99%. The composition may further comprise antimicrobial agents such as methyl paraben or propyl paraben. The composition may further comprise preservatives such as alpha-tocopherol or butylated hydroxytoluene (BHT). The composition may further comprise antioxidants. The antimicrobial agents, preservatives and antioxidants may be used alone or in combination.

In a preferred aspect of this embodiment, the composition consists essentially of a cannabinoid compound and between about 0.05 to about 5 wt % of an acid chosen from the group consisting of citric acid, ascorbic acid, malic acid, oxalic acid, succinic acid, tartaric acid, phosphoric acid, hydrochloric acid, nitric acid and sulphuric acid. Additional components (e.g. antimicrobial agents, preservatives, antioxidants) may comprise up to about 1 wt % of the composition. In an especially preferred embodiment, the composition of the invention consists essentially of (−)-$\Delta^9$-THC and between about 1 and about 2 wt % citric acid or phosphoric acid, wherein additional components comprise up to about 1 wt % of the solution.

Compositions according to this embodiment of the invention may be prepared by adding the acid to a solution of a cannabinoid compound in a solvent, mixing the solution, then evaporating the solution completely.

EXAMPLES

The following examples are illustrative but not limiting of the invention.
Starting Material:
In the examples below, the starting compositions were made using a synthesis technique for preparing a mixture of cannabinoids, including (−)-$\Delta^9$-trans-THC, as described in U.S. Pat. No. 7,186,850. In particular, step 1 of the synthesis process set forth in Example 4 of the '850 patent was followed to isolate (−)-$\Delta^9$-trans-THC and to provide sufficient purity for purification (i.e., no less than 80% by area (−)-$\Delta^9$-trans-THC, the specification for crude THC). The (−)-$\Delta^9$-trans-THC was then separated from the cannabinoid mixture by the method described in U.S. Pat. No. 7,449,589. In particular, the two-step purification process set forth in Example 3 of the '589 patent was followed to isolate (−)-$\Delta^9$-trans-THC and to provide a high purity (>99% (−)-$\Delta^9$-trans-THC) product.
Obtaining Results:
The results provided below and values provided herein were obtained using high performance liquid chromatography (HPLC) and thus are shown in terms of percent peak area. The HPLC operating parameters and conditions were as follows:
Column Waters Xterra RP-18, 150 mm×4.6 mm, 5 μm, C/N 186000492
Injection Volume 30 μL
Column Temperature 40° C.
Column Pressure 5000 psi setting
Eluent Pre-heater Connected
Sample Temperature 15° C.
Detection UV @ 228 nm
Flow Rate 1.2 mL/min
Mobile Phase A Water:Methanol (60:40 v/v)

Mobile Phase B 100% Methanol
Mobile Phase C Methanol:Ethanol (50:50 v/v)
Needle Wash 100% Ethanol (Absolute)
Column Wash Mobile Phase C—Methanol:Ethanol (50:50 v/v)
Analysis/Run Time 65 min

| Gradient Profile | Time (min) | % MP A | % MP B | %MP C |
|---|---|---|---|---|
| (Linear Gradient) | Initial | 100 | 0 | 0 |
| | 4 | 100 | 0 | 0 |

-continued

| Gradient Profile | Time (min) | % MP A | % MP B | %MP C |
|---|---|---|---|---|
| | 10 | 65 | 35 | 0 |
| | 14 | 45 | 55 | 0 |
| | 35 | 45 | 55 | 0 |
| | 45 | 5 | 95 | 0 |
| | 49 | 5 | 95 | 0 |
| | 51 | 0 | 100 | 0 |
| | 53 | 0 | 0 | 100 |
| | 58 | 0 | 0 | 100 |
| | 60 | 100 | 0 | 0 |
| | 65 | 100 | 0 | 0 |

In order to obtain weight percentages of CBN, $\Delta^8$-THC, and the impurity having a relative response time of 0.91 from the peak area percentages, the results for each impurity were divided by their respective measured relative response factors. The relative response factors for CBN and delta-8 THC have been determined by w/w % using qualified reference standards. The impurity at RRT=0.91 is still an unknown impurity for which no qualified reference standard exists. Therefore, a mass sensitive detector was utilized to determine the relative response factor to $\Delta^9$-THC. For example, the relative response factor of the impurity at RRT=0.91 is approximately 4 as determined by an ESA Ultra Charged Aerosol Detector (CAD) for an accurate mass response. The relative response factors for CBN and $\Delta^8$-THC to $\Delta^9$-THC at 228 nm have been determined by internal reference standards to be 2.43 and 0.87, respectively.

Storage Conditions:

The purified $(-)$-$\Delta^9$-trans-THC compositions were subjected to several different storage conditions, including: (i) freezer conditions at about $-15°$ C. to $-30°$ C. with no humidity control; (ii) refrigerated conditions at about $5°$ C. with no humidity control; (iii) ambient conditions of about $25°$ C. and 60% relative humidity; (iv) elevated temperature and humidity conditions of about $40°$ C. and about 75% relative humidity; and (iv) elevated temperature conditions of about $60°$ C. with no humidity control. Additionally, as described below, some samples contained various additives or excipients. The impurity limits against which the various examples were measured were based on the specifications described above.

Example 1

Ethanol in the high purity starting material was partially evaporated using vacuum distillation equipment [Vacuum Pump, Busch LLC, Virginia Beach, Va., Condenser, Rubicon Industries Corp., Brooklyn, N.Y.] such that the $(-)$-$\Delta^9$-trans-THC was concentrated between 3.0% by weight and 7.0% by weight. The composition was placed in Class 3 amber glass bottles obtained from Qorpak Corp. (Bridgeville, Pa.), sparged with carbon dioxide ($CO_2$) gas, and stored under freezer conditions ($-15°$ C. to $-30°$ C.). After 24 months, the purity of the composition was determined to be as follows:

| | % Peak Areas according to Relative Retention Time (RRT) | | | | | | | | | | | | |
|---|---|---|---|---|---|---|---|---|---|---|---|---|---|
| Sample | 0.61 | 0.63 | 0.64 | 0.68 | 0.70 | 0.80 | 0.85 | 0.91* | CBN* | $\Delta^9$-THC | $\Delta^8$-THC* | 1.32 | 1.51 |
| D1150-070801B | <0.1 | <0.1 | <0.1 | <0.1 | <0.1 | <0.1 | <0.1 | <0.1 | <0.1 | 99.5 | <0.1 | <0.1 | <0.1 |
| D1150-070901B | <0.1 | <0.1 | <0.1 | <0.1 | <0.1 | <0.1 | <0.1 | <0.1 | <0.1 | 99.6 | <0.1 | <0.1 | <0.1 |
| D1150-0701001B | <0.1 | <0.1 | <0.1 | <0.1 | <0.1 | <0.1 | <0.1 | <0.1 | <0.1 | 99.6 | <0.1 | <0.1 | <0.1 |

The initial (T=0) chromatographic purity values (using percent peak area) for lots -070801B, -070901B, and -0701001B were measured at 99.7%, 99.7%, and 99.8%, respectively. Thus, for lots -070801B, -070901B, and -0701001B, respectively 99.8%, 99.9%, and 99.8% by area of the $(-)$-$\Delta^9$-trans-THC remained in undegraded form after exposure of the composition to these storage conditions. The three samples were determined to meet ICH quality requirements after 24 months.

Example 2

As in Example 1, ethanol in the high purity starting material was partially evaporated using vacuum distillation equipment to achieve a concentration of $(-)$-$\Delta^9$-trans-THC of about 3-7% by weight. Then, the partially evaporated starting material and citric acid dissolved in ethanol were added to degassed USP/NF quality refined sesame oil obtained from Jeen International Corp. (Fairfield, N.J.) and fortified with the additives butylated hydroxytoluene (BHT), methyl paraben, propyl paraben and α-tocopherol to concentrations ranging from about 0.15% to 0.25% by weight, about 0.15% to 0.25% by weight, about 0.038% to 0.063% by weight, and about 0.38% to 0.63% by weight, respectively. The ethanol in the mixture was then further evaporated using a rotary evaporator (Bucchi, Flawil, Switzerland) to less than about 0.5% by weight of the mixture. The concentrations of the citric acid and $(-)$-$\Delta^9$-trans-THC were about 0.1% and about 6-7% by weight, respectively, in the final mixture.

The composition was then placed in narrow neck Class 1 low actinic, borosilicate glass bottles with polyethylene caps obtained from Corning Inc. (Corning, N.Y.) under an inert atmosphere of argon. The glass bottles were filled with the composition to about the base of the neck of the bottles. The composition was then subjected to storage conditions of $25°$ C. and 60% relative humidity for 24 months after which the samples were analyzed. The results of the stability test were as follows:

| | % Peak Areas according to Relative Retention Time (RRT) | | | | | | | | | | | |
|---|---|---|---|---|---|---|---|---|---|---|---|---|
| Sample | 0.61 | 0.63 | 0.64 | 0.68 | 0.70 | 0.85 | 0.91* | CBN* | $\Delta^9$-THC | $\Delta^8$-THC* | 1.32 | 1.51 |
| D1161-051201 | 0.06 | 0.02 | | 0.02 | 0.03 | 0.12 | 0.28 | 0.27 | 98.94 | 0.20 | 0.06 | |
| D1161-051203 | 0.18 | 0.02 | | 0.02 | 0.03 | 0.10 | 0.35 | 0.28 | 98.73 | 0.21 | 0.06 | 0.02 |
| D1161-051204 | 0.05 | 0.02 | 0.02 | 0.02 | 0.03 | 0.12 | 0.28 | 0.33 | 98.87 | 0.20 | 0.05 | |

The three samples were determined to meet ICH quality requirements after 24 months at 25° C. and 60% relative humidity.

Example 3

As in Examples 1 and 2, ethanol in the high purity starting material was partially evaporated using vacuum distillation equipment to achieve a concentration of (−)-$\Delta^9$-trans-THC of about 3-7% by weight. Then, the partially evaporated starting material and citric acid in ethanol were added to degassed USP/NF quality refined sesame oil from Jeen International Corp. (Fairfield, N.J.). The percentage of dissolved oxygen in the oil was determined to be 1.93% after degassing using a Centrifan™ evaporator from Modular SFC, Inc. (Franklin, Mass.) in an inert atmosphere of nitrogen. The ethanol in the mixture was then further evaporated using a Centrifan™ evaporator from Modular SFC, Inc. (Franklin, Mass.) in an inert atmosphere of nitrogen to 0.74% by weight. The concentrations of the citric acid and (−)-$\Delta^9$-trans-THC were about 0.001% and about 5.6% by weight, respectively, in the final mixture.

The composition was then placed in a Class 1, narrow-necked, amber, borosilicate glass bottles with polyethylene caps obtained from West Pharmaceutical Services, Inc. (Lionville, Pa.) under an inert atmosphere of nitrogen. The glass bottles were filled with the composition into the neck of the bottles. Then, the filled glass bottles were placed in Pakdry 1500 Mylar® bags obtained from Impak Corp. (Los Angeles, Calif.) which with Oxyfree 504 oxygen absorber packs from Impak Corp. after which the bags were vacuum sealed. The composition was then subjected to storage conditions of about 60° C. and no humidity control for four weeks and then analyzed. The results of the stability test were as follows:

trans-THC of about 3-7% by weight. Then, the partially evaporated starting material and citric acid were added to degassed USP/NF quality refined sesame oil from Jeen International Corp. (Fairfield, N.J.) fortified with the additives BHT, methyl paraben, propyl paraben, and α-tocopherol to concentrations ranging from about 0.15% to 0.25% by weight, about 0.15% to 0.25% by weight, about 0.038% to 0.063% by weight, and about 0.38% to 0.63% by weight, respectively. The ethanol in the mixture was then further evaporated using a rotary evaporator (Bucchi, Flawil, Switzerland) to less than 0.5% by weight. The concentrations of the citric acid and (−)-$\Delta^9$-trans-THC were about 0.1% and about 6-7% by weight, respectively, in the final mixture.

The composition was then placed in narrow neck Class 1 low actinic, borosilicate glass bottles obtained from Corning Inc. (Corning, N.Y.) under an inert atmosphere of argon. The glass bottles were filled with the composition to about the base of the neck of the bottles. The composition was then subjected to refrigerated conditions of about 5° C. to about 8° C. without any humidity control for 36 months after which the samples were analyzed. The results of the stability test were as follows:

| | % Peak Areas according to Relative Retention Time (RRT) | | | | |
|---|---|---|---|---|---|
| Sample | 0.60 | 0.85 | CBN* | $\Delta^9$-THC | $\Delta^8$-THC* |
| D1161-051203 | 0.1 | 0.1 | 0.2 | 99.5 | 0.1 |
| D1161-051204 | 0.2 | 0.1 | 0.2 | 99.4 | 0.1 |
| D1161-060101 | 0.1 | 0.1 | 0.2 | 99.5 | 0.1 |

| | % Peak Areas according to Relative Retention Time (RRT) | | | | | | | | | | | | | | | | |
|---|---|---|---|---|---|---|---|---|---|---|---|---|---|---|---|---|---|
| Sample at 60° C. | 0.56 | 0.57 | 0.60 | 0.62 | 0.63 | 0.65 | 0.68 | 0.70 | 0.73 | 0.76 | 0.78 | 0.85 | 0.91 * | CBN * | $\Delta^9$-THC | $\Delta^8$-THC * | 1.08 |
| 4 weeks | 0.01 | 0.01 | 0.12 | 0.01 | 0.02 | 0.01 | 0.04 | 0.01 | 0.01 | 0.01 | 0.02 | 0.02 | 0.31 | 0.15 | 99.18 | 0.04 | 0.04 |
| 3 months | | 0.01 | 0.15 | 0.01 | 0.01 | 0.01 | 0.06 | | | | | 0.02 | 0.45 | 0.22 | 98.99 | 0.03 | 0.05 |

The initial assay of (−)-$\Delta^9$-trans-THC was determined to be 5.60% by weight by the USP assay for THC. After three months, the assay was 5.47% by weight or 97.7% of its initial potency (i.e., in undegraded form). As shown in the above tabulated data, the sample met ICH quality requirements after three months of accelerated exposure conditions.

Example 4

As in the previous Examples, ethanol in the high purity starting material was partially evaporated using vacuum distillation equipment to achieve a concentration of (−)-$\Delta^9$-

The initial (T=0) and 36 month measured potency values for lot -051203 was 6.8% and 6.5%, respectively; for lot -051204 was 7.0 and 6.6, respectively; and for lot -006101 was 6.9% and 6.6%, respectively, again by the USP assay for THC. Thus, after these storage conditions, 95.6% of the (−)-$\Delta^9$-trans-THC remained in undegraded form for lot -051203, 94.3% of the (−)-$\Delta^9$-trans-THC remained in undegraded form for lot -051204, and 95.6% of the (−)-$\Delta^9$-trans-THC remained in undegraded form for lot -006101. As shown in the above table, the three samples all met ICH quality requirements after 36 months of exposure to refrigerated conditions.

Example 5

As in the previous Examples, ethanol in the high purity starting material was partially evaporated using vacuum distillation equipment to achieve a concentration of $(-)\text{-}\Delta^9$-trans-THC of about 3-7% by weight. Then the starting material was placed in a freezer and maintained at a temperature below about $-15°$ C. The material was then sparged with $CO_2$ for several minutes prior to packaging. Then, citric acid was combined with several samples of the material to achieve different concentrations of acid ranging from about 0.0001 to 0.1% (1 ppm to 1000 ppm). Subsequently, refined USP/NF quality sesame oil from Jeen International Corp. (Fairfield, N.J.) was added to the mixture. The ethanol was then further evaporated from the mixture using a Centrifan™ evaporator from Modular SFC, Inc. (Franklin, Mass.) in an inert atmosphere of nitrogen. This final composition contained, by weight, about 94% sesame oil and 6% $(-)\text{-}\Delta^9$-trans-THC as well as about 0.2% ethanol and citric acid having concentrations of about 0.0001% (1 ppm), 0.001% (10 ppm) and 0.1% (1000 ppm).

The composition was bottled in a narrow-necked, low actinic, Class 1 borosilicate glass bottle under an inert atmosphere of nitrogen. The glass bottles, made of low actinic Pyrex® glass with orange polypropylene caps from Corning Inc., were filled with the composition after which the bottles were sealed. Finally, the filled and sealed glass bottles were placed in Pakdry 1500 Mylar® bags with Oxyfree 504 oxygen absorber packs from Impak Corp. after which the bags were vacuum heat sealed.

The composition was subjected to storage conditions of 40° C. and 75% relative humidity for nine months and then tested as described above:

| Citric Acid Added | % Peak Areas according to Relative Retention Time (RRT) | | | | | | | | | | | | | | | |
|---|---|---|---|---|---|---|---|---|---|---|---|---|---|---|---|---|
| | 0.56 | 0.57 | 0.60 | 0.62 | 0.63 | 0.65 | 0.68 | 0.78 | 0.83 | 0.85 | 0.87 | 0.91* | CBN* | delta-9 THC | delta-8 THC* | 1.08 |
| Study#2 (1 ppm) | 0.05 | 0.06 | 0.01 | 0.12 | 0.01 | 0.14 | 0.16 | 0.04 | | 0.03 | | | 0.84 | 0.17 | 97.39 | 0.86 | 0.12 |
| Study#3 (10 ppm) | 0.03 | 0.03 | 0.11 | 0.19 | 0.09 | | 0.12 | 0.05 | | 0.03 | | | 0.60 | 0.38 | 97.54 | 0.76 | 0.07 |
| Study#5a (1000 ppm) | 0.02 | 0.04 | 0.05 | 0.06 | 0.02 | 0.03 | 0.11 | 0.07 | 0.02 | 0.03 | | 0.85 | 1.18 | | 97.33 | 0.09 | 0.09 |

The composition was also tested after twelve months under the same storage conditions, the results of which are shown below:

| Citric Acid Added (ppm) | % Peak Areas according to Relative Retention Time (RRT) | | | | | | | | | | | | | | | | |
|---|---|---|---|---|---|---|---|---|---|---|---|---|---|---|---|---|---|
| | 0.59 | 0.60 | 0.62 | 0.63 | 0.65 | 0.67 | 0.68 | 0.70 | 0.72 | 0.79 | 0.84 | 0.86 | 0.91 * | CBN | delta-9 THC | delta-8 THC | 1.08 |
| Study#2 (1 PPM) | 0.04 | 0.01 | 0.05 | 0.01 | 0.12 | | 0.14 | 0.08 | 0.05 | 0.04 | | 0.07 | 0.94 | 0.18 | 96.74 | 1.50 | |
| Study#3 (10 PPM) | 0.02 | 0.04 | | 0.06 | 0.18 | | 0.08 | | 0.10 | 0.02 | | 0.06 | 0.69 | 0.37 | 97.30 | 1.04 | |
| Study#5a (1000 PPM) | 0.03 | 0.05 | 0.01 | 0.05 | 0.02 | | 0.01 | 0.06 | 0.07 | 0.06 | 0.01 | 0.04 | 0.87 | 1.21 | 97.37 | 0.05 | 0.04 |

The initial (T=0) chromatographic purity values (using percent peak area) for Study #2, Study #3, and Study #5a were measured at 99.74%, 99.77%, and 99.79%, respectively. Thus, for Study #2, Study #3, and Study #5a, the percentages by area of the $(-)\text{-}\Delta^9$-trans-THC that remained in undegraded form after exposure of the composition to these storage conditions at nine months were, respectively, 97.6%, 97.8%, and 97.5%. Similarly, for Study #2, Study #3, and Study #5a, the percentages by area of the $(-)\text{-}\Delta^9$-trans-THC that remained in undegraded form after exposure of the composition to these storage conditions at twelve months were, respectively, 97.0%, 97.5%, and 97.6%. As shown in the above tables, the three samples all met ICH quality requirements after nine and twelve months of storage at 40° C. and 75% relative humidity.

The composition was also tested after twenty-six months at 25° C. and 60% relative humidity storage conditions, the results of which are shown below:

| Citric Acid | % Peak Areas according to Relative Retention Time (RRT) | | | | | | | | | | | | | | | | |
|---|---|---|---|---|---|---|---|---|---|---|---|---|---|---|---|---|---|
| Added (ppm) | 0.60 | 0.61 | 0.62 | 0.64 | 0.65 | 0.66 | 0.69 | 0.71 | 0.73 | 0.77 | 0.81 | 0.87 | 0.92 * | CBN | delta-9 THC | delta-8 THC | 1.07 |
| Study#2 (1 PPM) | | 0.05 | 0.02 | 0.06 | 0.03 | 0.09 | 0.16 | 0.12 | 0.04 | 0.03 | 0.04 | 0.05 | 0.73 | 0.17 | 97.55 | 0.85 | 0.02 |
| Study#3 (10 PPM) | | 0.06 | 0.04 | 0.05 | 0.03 | 0.05 | 0.16 | 0.09 | 0.07 | 0.03 | 0.03 | 0.06 | 0.55 | 0.36 | 97.53 | 0.87 | 0.01 |
| Study#5a (1000 PPM) | 0.01 | 0.01 | 0.01 | 0.01 | 0.04 | 0.06 | 0.03 | 0.10 | 0.09 | 0.03 | 0.06 | 0.02 | 0.52 | 0.71 | 98.20 | 0.04 | 0.03 |

The initial (T=0) chromatographic purity values (using percent peak area) for Study #2, Study #3, and Study #5a were measured at 99.74%, 99.77%, and 99.79%, respectively. Thus, for Study #2, Study #3, and Study #5a, the percentages by area of the $(-)$-$\Delta^9$-trans-THC that remained in undegraded form after exposure of the composition to these storage conditions at 26 months were, respectively, 97.6%, 97.5%, and 98.2%. As shown in the above tables, the three samples all met ICH quality requirements after twenty-six months of storage at 25° C. and 60% relative humidity.

relative humidity for 12 months and then tested as described above:

| | % Peak Areas according to Relative Retention Time (RRT) | | | | | | | | | | | | | | |
|---|---|---|---|---|---|---|---|---|---|---|---|---|---|---|---|
| Temp | 0.56 | 0.57 | 0.60 | 0.62 | 0.63 | 0.65 | 0.68 | 0.70 | 0.78 | 0.85 | 0.91* | CBN* | delta-9 THC | delta-8 THC* | 1.08 |
| 5-1 25° C., 60% | 0.03 | | 0.03 | 0.07 | 0.03 | 0.06 | 0.02 | 0.04 | 0.02 | 0.08 | 0.24 | 0.53 | 98.63 | 0.20 | |
| 5-2 40° C., 75% | 0.00 | 0.02 | 0.05 | 0.07 | 0.01 | 0.02 | 0.04 | 0.07 | 0.04 | 0.05 | 0.86 | 1.23 | 97.34 | 0.09 | 0.10 |

The initial (T=0) chromatographic purity value (using percent peak area) for the study was 99.69%. Thus, for Study 5-1, the percent by area of the $(-)$-$\Delta^9$-trans-THC that remained in undegraded form after exposure of the composition to 25° C. and 60% relative humidity for twelve months was 98.9%. Similarly, for Study 5-2, the percent by area of the $(-)$-$\Delta^9$-trans-THC that remained in undegraded form after exposure of the composition to 40° C. and 75% relative humidity for twelve months was 97.6%. As shown in the above table, the samples all met ICH quality requirements after 12 months of storage at 40° C. and 75% relative humidity.

Example 6

As in the previous Examples, ethanol in the high purity starting material was partially evaporated using vacuum distillation equipment to achieve a concentration of $(-)$-$\Delta^9$-trans-THC of about 3-7% by weight. Then the starting material was placed in a freezer and maintained at a temperature below about −15° C. The material was then sparged with $CO_2$ for several minutes prior to packaging. Then, citric acid was combined with several samples of the material to achieve different concentrations of acid ranging from about 0.0001 to 0.1% (1 ppm to 1000 ppm). Subsequently, refined USP/NF quality sesame oil from Jeen International Corp. (Fairfield, N.J.) fortified with methylparaben, propylparaben, BHT, alpha-tocopherol in amounts of about 0.2% by weight, 0.05% by weight, 0.2% by weight, and 0.5% by weight, respectively, was added to the mixture. Then, this mixture was partially evaporated at 30° C. using a rotor evaporator from Buchi, Inc. (Flawil, Switzerland). The final composition contained, by weight, about 93.5% sesame oil, 6.5% $(-)$-$\Delta^9$-trans-THC, 0.01% ethanol; 0.1% citric acid; 0.2% methylparaben; 0.05% propylparaben; 0.2% BHT; and 0.5% alpha-tocopherol.

The composition was bottled in a narrow-necked, low actinic, Class 1 borosilicate glass bottle under an inert atmosphere of nitrogen. The bottles, made of low actinic, Pyrex® glass and having orange polypropylene caps, were filled with the composition to at about 100% full after which the bottles were sealed.

The composition was subjected to storage conditions of 25° C. and 60% relative humidity and at 40° C. and 75%

Example 7

According to this Example 7, a composition consisting essentially of a cannabinoid and an acid was prepared and tested for stability.

Composition Preparation:

A citric acid solution was made by dissolving 128 mg of anhydrous citric acid in 20 ml of ethanol (the concentration of the citric acid was 6.41 mg/ml), while a phosphoric acid solution was made by dissolving 140 mg of 85% phosphoric acid in 20 ml of ethanol (the concentration of the citric acid was 7.00 mg/ml). 1 ml samples of each of the acid solutions were added to 10 ml samples of a solution of $(-)$-$\Delta^9$-THC in ethanol (the concentration of the $(-)$-$\Delta^9$-THC was 41.9 mg/ml). The acid and $(-)$-$\Delta^9$-THC solutions were mixed and then evaporated to dryness under a fine stream of nitrogen. The control sample was made by evaporating a solution of $(-)$-$\Delta^9$-THC in ethanol to dryness without adding any acid.

TABLE 1

Compositions 1-3

| | Acid | Other components |
|---|---|---|
| Composition 1 | None | None |
| Composition 2 | 1.5 wt % citric acid | None |
| Composition 3 | 1.5 wt % phosphoric acid | None |

Stability:

The stability of the compositions was assessed at three different conditions: room temperature (RT), about 5° C. or refrigerated conditions (RF) and about −15° C. or frozen conditions (FZ). The degradation of the (−)-$\Delta^9$-THC was monitored using the HPLC method with ultraviolet detection at 228 nm and all other parameters as set forth above. Two samples for analysis by HPLC were prepared for each composition by transferring approx. 2-5 mg of the compositions into a container and adding sufficient ethanol to form a solution with a concentration of 0.6-0.7 mg/ml of (−)-$\Delta^9$-THC. Each detected impurity peak was measured using percent peak area (% PA) with respect to the peak area counts for (−)-$\Delta^9$-THC for each chromatogram, i.e. the degradation of the composition was assessed against (−)-$\Delta^9$-THC not against a branded product containing (−)-$\Delta^9$-THC. Each impurity peak was identified with a RRT relative to the (−)-$\Delta^9$-THC peak elution time from each chromatogram. Impurity peaks measuring above 0.05% peak area were recorded and the average RRT of the two samples was recorded (see Table 2 below).

Table 2 shows the results of the stability tests for the compositions. The period of time after which the degradation of the composition was assessed is indicated beside each table.

TABLE 2

Stability tests for compositions 1-3

% Peak Areas according to Relative Retention Time (RRT)

| Condition | 0.56 | 0.57 | 0.60 | 0.61 | 0.63 | 0.65 | 0.68 | 0.73 | 0.80 | 0.85 | 0.90 | 0.94 | 1.06 |
|---|---|---|---|---|---|---|---|---|---|---|---|---|---|
| Composition 1, 3 months | | | | | | | | | | | | | |
| RT |  | 1.14 | 0.56 | 0.41 | 2.40 | 1.24 | 4.71 | 0.55 | 0.29 | 0.03 | 0.03 | 9.99 | 1.04 |
| RF |  | 0.14 | 0.28 | 0.08 | 0.63 | 2.39 | 0.02 | 0.48 | 0.15 | 0.03 | 0.04 | 0.83 | 0.16 |
| FZ |  | 0.09 |  | 0.02 | 0.08 | 0.93 |  | 0.29 | 0.10 | 0.02 | 0.02 | 0.03 | 0.05 |
| Composition 2, 3 months | | | | | | | | | | | | | |
| RT |  |  | 0.38 |  | 0.06 |  | 0.03 |  |  | 0.09 | 0.02 | 0.23 | 0.07 |
| RF | 0.02 | 0.26 | 1.73 |  | 0.28 | 0.36 | 0.15 |  | 0.10 | 0.05 |  | 1.11 |  |
| FZ | 0.12 | 0.02 | 0.71 |  | 0.08 | 0.08 | 0.09 |  | 0.04 | 0.04 |  | 0.18 | 0.03 |
| Composition 3, 3 months | | | | | | | | | | | | | |
| RT |  | 1.22 | 0.26 | 0.91 | 0.31 | 0.37 | 1.02 | 0.03 | 0.21 | 0.03 | 0.37 | 5.36 | 5.56 |
| RF |  |  | 0.65 | 2.02 | 0.26 |  | 0.13 |  | 0.09 | 0.06 |  | 1.32 | 0.16 |
| FZ |  |  | 0.83 |  | 0.12 |  | 0.04 |  | 0.03 | 0.04 | 0.04 | 0.36 | 0.07 |

Table 2 shows that considerable degradation of the composition not containing any acid (composition 1) occurred during the observation period, especially in view of the quantity of cannabinol formed. By contrast, the degradation observed for the composition containing citric acid (composition 2) was less. The composition containing phosphoric acid (composition 3) did not show as much of an improvement in comparison to the composition containing citric acid; however, the inventors believe that this acid may provide a greater improvement if used at another concentration.

The invention claimed is:

1. A composition comprising a cannabinoid, an acid, an oil, and a pharmaceutically-acceptable solvent in a concentration of between about 0.001% by weight and about 2% by weight, wherein the solvent comprises a $C_1$-$C_4$ alcohol, the acid is sufficiently soluble in the solvent to provide an amount of dissolved acid in the solvent which improves the stability of the composition and the composition is in liquid form.

2. The composition of claim 1, wherein the composition has a purity profile by HPLC of no more than about 2.0% by weight of $\Delta^8$-THC; no more than about 0.5% by weight of cannabinol; no more than about 0.2% by mass of the impurity having a relative retention time of 0.91; no more than about 0.2% by area of individual unspecified impurities; and no more than about 2.5% total impurities by summing the percent weights of $\Delta^8$-THC and cannabinol, the percent mass of the impurity having a relative retention time of 0.91, and the percent areas of the individual unspecified impurities, after exposure of the composition to storage conditions selected from the group consisting of: (i) refrigerated conditions of between about 5° C. to about 8° C. for 36 months; (ii) ambient conditions of about 25° C. and about 60% relative humidity for 24 months; (iii) elevated temperature conditions of about 40° C. and 75% relative humidity for nine months; and (iv) elevated temperature conditions of about 60° C. for 4 weeks.

3. The composition of claim 1, wherein the cannabinoid comprises a tetrahydrocannabinol compound.

4. The composition of claim 3, wherein the tetrahydrocannabinol compound comprises (−)-$\Delta^9$-trans-tetrahydrocannabinol.

5. The composition of claim 2, wherein the cannabinoid comprises (−)-$\Delta^9$-trans-tetrahydrocannabinol and the storage conditions are the refrigerated conditions of between about 5° C. to about 8° C. for 36 months.

6. The composition of claim 2, wherein the cannabinoid comprises (−)-$\Delta^9$-trans-tetrahydrocannabinol and the storage conditions are the ambient conditions of about 25° C. and about 60% relative humidity for 24 months.

7. The composition of claim 2, wherein the cannabinoid comprises (−)-$\Delta^9$-trans-tetrahydrocannabinol and the storage conditions are the elevated temperature conditions of about 40° C. and 75% relative humidity for nine months.

8. The composition of claim 2, wherein the cannabinoid comprises (−)-$\Delta^9$-trans-tetrahydrocannabinol and the storage conditions are the elevated temperature conditions of about 60° C. for 4 weeks.

9. The composition of claim 1, wherein the $C_1$-$C_4$ alcohol comprises ethanol.

10. The composition of claim 1, wherein the concentration of the $C_1$-$C_4$ alcohol is between about 0.1% by weight to about 1% by weight.

11. The composition of claim 1, wherein the oil is selected from the group consisting of a vegetable oil, a fish oil, and an animal fat.

12. The composition of claim 1, wherein the oil is selected from the group consisting of: almond oil; babassu oil; borage oil; blackcurrant seed oil; canola oil; castor oil; coconut oil; corn oil; cottonseed oil; evening primrose oil; grapeseed oil; groundnut oil; mustard seed oil; olive oil; palm oil; palm kernel oil; peanut oil; rapeseed oil; safflower oil; sesame oil; shark liver oil; soybean oil; and sunflower oil; and mixtures thereof.

13. The composition of claim 11, wherein the concentration of the oil in the composition is at least about 90% by weight.

14. The composition of claim 1, wherein the acid is a weak acid.

15. The composition of claim 14, wherein the weak acid is selected from the group consisting of a fatty acid, citric acid, oxalic acid, succinic acid, tartaric acid, acetic acid, lactic acid, salicylic acid, carbonic acid and phosphoric acid and mixtures thereof.

16. The composition of claim 1, wherein the concentration of the acid in the composition is between about 0.1 ppm to about 10,000 ppm.

17. The composition of claim 16, wherein the concentration of the acid in the composition is between about 10 ppm to about 100 ppm.

18. The composition of claim 1, wherein the solvent comprises ethanol and the acid comprises carbonic acid.

19. The composition of claim 11, wherein the oil comprises sesame oil.

20. The composition of claim 19, wherein the sesame oil is unrefined and contains the acid.

21. The composition of claim 20, wherein the acid comprises a free fatty acid.

22. The composition of claim 11, wherein the cannabinoid comprises $(-)$-$\Delta^9$-trans-tetrahydrocannabinol, the oil comprises sesame oil, the solvent comprises ethanol, and the acid comprises citric acid.

23. The composition of claim 22 further comprising at least one of antimicrobial agents, preservatives, and antioxidants.

24. The composition of claim 1, wherein the cannabinoid is $(-)$-$\Delta^9$-trans-tetrahydrocannabinol and the composition has an initial purity of $(-)$-$\Delta^9$-trans-tetrahydrocannabinol by HPLC of at least about 97.5% by area and has a stability such that at least about 95% by area of the $(-)$-$\Delta^9$-trans-tetrahydrocannabinol remains in undegraded form after exposure of the composition to storage conditions selected from the group consisting of at least one of: (i) ambient conditions of about 25° C. and about 60% relative humidity for twelve months; and (ii) elevated temperature conditions of about 40° C. and 75% relative humidity for nine months.

25. The composition of claim 24, wherein the initial purity of $(-)$-$\Delta^9$-trans-tetrahydrocannabinol by HPLC is at least about 99% by area and the stability is such that at least about 97.5% by area of the $(-)$-$\Delta^9$-trans-tetrahydrocannabinol remains in undegraded form after exposure of the composition to the storage conditions.

26. The composition of claim 24, wherein the storage conditions are the ambient conditions of about 25° C. and about 60% relative humidity for twelve months.

27. The composition of claim 24, wherein the storage conditions are the elevated temperature conditions of about 40° C. and 75% relative humidity for nine months.

28. The composition of claim 1, wherein the cannabinoid is $(-)$-$\Delta^9$-trans-tetrahydrocannabinol and the composition has an initial purity of $(-)$-$\Delta^9$-trans-tetrahydrocannabinol by HPLC of at least about 97.5% by area and has a stability such that at least about 95% by area of the $(-)$-$\Delta^9$-trans-tetrahydrocannabinol remains in undegraded form after exposure of the composition to storage conditions of elevated temperature conditions of about 40° C. and 75% relative humidity for twelve months.

29. A composition comprising $(-)$-$\Delta^9$-trans-tetrahydrocannabinol, sesame oil, a solvent comprising ethanol in a concentration of between about 0.001% by weight and about 2% by weight, and citric acid, wherein the amount of ethanol is sufficient to dissolve at least a portion of the citric acid such that the composition is stable at room temperature for 24 months and the composition is in liquid form.

30. The composition of claim 29, wherein the concentration of the $(-)$-$\Delta^9$-trans-tetrahydrocannabinol in the composition is between about 3% to about 7% by weight.

31. A dosage form comprising: (a) the composition of claim 1; and (b) a capsule encapsulating the composition.

32. A dosage form comprising: (a) the composition of claim 29; and (b) a capsule encapsulating the composition.

* * * * *

UNITED STATES PATENT AND TRADEMARK OFFICE
CERTIFICATE OF CORRECTION

Page 1 of 1

PATENT NO. : 8,980,940 B2
APPLICATION NO. : 13/302289
DATED : March 17, 2015
INVENTOR(S) : Ronald Rossi et al.

It is certified that error appears in the above-identified patent and that said Letters Patent is hereby corrected as shown below:

On the Title page, should read 34 claims, no drawings

In the Claims

At column 30, line 42, please insert the following claims 33 and 34.

--33. The composition of claim 1, wherein the cannabinoid comprises cannabidiol.

34. A dosage form comprising: (a) the composition of claim 33; and (b) a capsule encapsulating the composition.--

Signed and Sealed this
Eighth Day of September, 2015

Michelle K. Lee
*Director of the United States Patent and Trademark Office*